US008163162B2

(12) United States Patent  (10) Patent No.: US 8,163,162 B2
Chatelier et al.  (45) Date of Patent: Apr. 24, 2012

(54) METHODS AND APPARATUS FOR ANALYZING A SAMPLE IN THE PRESENCE OF INTERFERENTS

(75) Inventors: Ronald C. Chatelier, Bayswater (AU); Alastair McIndoe Hodges, Blackburn South (AU); Bruce Verity, Narre Warren (AU)

(73) Assignee: LifeScan, Inc., Milpitas, CA (US)

( * ) Notice: Subject to any disclaimer, the term of this patent is extended or adjusted under 35 U.S.C. 154(b) by 1421 days.

(21) Appl. No.: 11/278,341

(22) Filed: Mar. 31, 2006

(65) Prior Publication Data

US 2007/0227912 A1 Oct. 4, 2007

(51) Int. Cl.
 *G01N 27/327* (2006.01)
(52) U.S. Cl. .................. 205/792; 205/775
(58) Field of Classification Search .......... 204/403.01–403.14, 415, 416, 204/408, 450–455, 600–605; 205/777.5–779, 205/775, 792; 435/817
 See application file for complete search history.

(56) References Cited

U.S. PATENT DOCUMENTS

| 5,496,453 | A  | * | 3/1996  | Uenoyama et al. ...... 205/777.5 |
| 6,193,873 | B1 |   | 2/2001  | Ohara et al. |
| 6,379,513 | B1 |   | 4/2002  | Chambers et al. |
| 6,576,117 | B1 | * | 6/2003  | Iketaki et al. ........ 205/777.5 |
| 6,599,407 | B2 | * | 7/2003  | Taniike et al. ........ 204/403.1 |
| 6,632,349 | B1 |   | 10/2003 | Hodges et al. |
| 6,676,995 | B2 |   | 1/2004  | Dick et al. |
| 6,689,411 | B2 |   | 2/2004  | Dick et al. |
| 6,749,887 | B1 |   | 6/2004  | Dick et al. |
| 6,780,645 | B2 |   | 8/2004  | Hayter et al. |
| 2004/0120848 | A1 | | 6/2004 | Teodorczyk |
| 2005/0176153 | A1 | | 8/2005 | O'hara et al. |
| 2007/0074977 | A1 | * | 4/2007 | Guo et al. .................. 205/792 |

FOREIGN PATENT DOCUMENTS

| DE | 43 35 241       |   | 4/1995  |
| EP | 1 236 995       |   | 9/2002  |
| EP | 1 467 206       |   | 10/2004 |
| WO | WO-01/57510     |   | 8/2001  |
| WO | 2005/045415 A1  |   | 5/2005  |
| WO | 2005/045417 A1  |   | 5/2005  |
| WO | WO2005045412    | * | 5/2005  |

OTHER PUBLICATIONS

Australian Examiner's First Report on Patent Application No. 2007201378, dated Jun. 18, 2008.
Notice of Acceptance, Australian Patent Application No. 2007201378, dated Aug. 25, 2009.
Examiner's Requisition, Canadian Application No. 2,582,952, dated May 19, 2009.
Examiner's Requisition, Canadian Application No. 2,582,952, dated Feb. 19, 2010.

(Continued)

*Primary Examiner* — Alex Noguerola
*Assistant Examiner* — Gurpreet Kaur
(74) *Attorney, Agent, or Firm* — Nutter McClennen & Fish LLP

(57) ABSTRACT

Disclosed herein are methods and apparatus for determining analyte concentration in a rapid and accurate manner. The methods include depositing a physiological sample in an electrochemical cell and finding a first and second current transient. Peak current values are obtained from the first and second peak current values and used to reduce the influence of interferents in a current value. Based on this "corrected" current value, an accurate analyte concentration can be determined.

14 Claims, 10 Drawing Sheets

OTHER PUBLICATIONS

European Search Report and Written Opinion, European Application No. 101806990.0, dated Nov. 23, 2010.
European Search Report and Written Opinion, European Application No. 10180719.6, dated Nov. 18, 2010.
European Search Report and Written Opinion, European Application No. 10180741.0, dated Nov. 18, 2010.
Japanese Office Action issued Oct. 4, 2011 in Japanse Application No. 2007-087635.

* cited by examiner

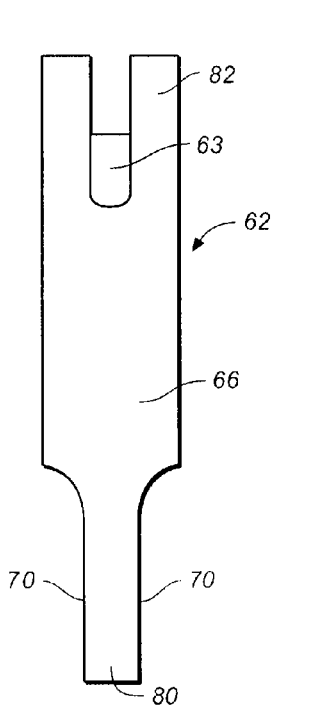
FIG. 2
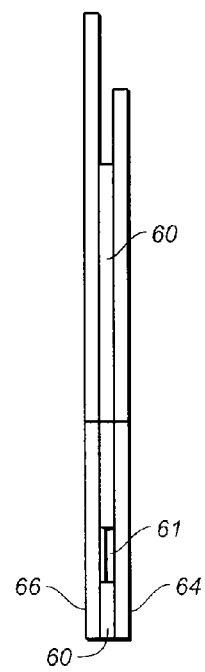
FIG. 3
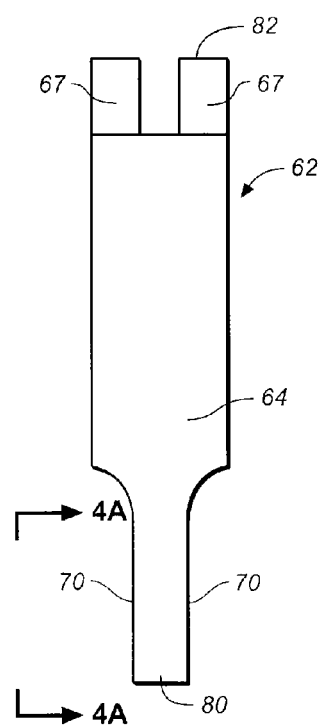
FIG. 4A
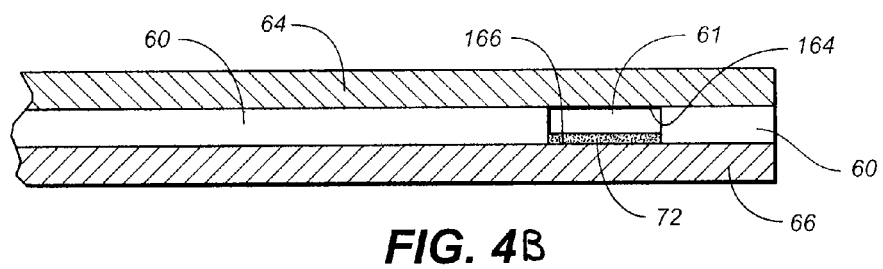
FIG. 4B

METHODS AND APPARATUS FOR ANALYZING A SAMPLE IN THE PRESENCE OF INTERFERENTS

BACKGROUND OF THE INVENTION

Electrochemical glucose test strips, such as those used in the OneTouch® Ultra® whole blood testing kit, which are available from LifeScan, Inc., are designed to measure the concentration of glucose in a blood sample from patients with diabetes. The measurement of glucose is based upon the specific oxidation of glucose by the flavo-enzyme glucose oxidase ($GOx_{(ox)}$). During this reaction, the enzyme becomes reduced which is denoted as ($GOx_{(red)}$). The enzyme is re-oxidized by reaction with the oxidized mediator ferricyanide ($Fe(CN)_6^{3-}$), which is itself reduced during the course or the reaction. These reactions are summarized below.

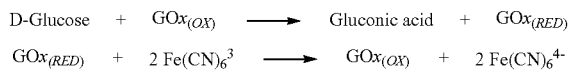

When the reaction set forth above is conducted with a test potential applied between two electrodes, an electrical current may be created by the electrochemical re-oxidation of the reduced mediator (ferrocyanide or $Fe(CN)_6^{4-}$) at the electrode surface. Thus, since, in an ideal environment, the amount of ferrocyanide created during the chemical reaction described above is directly proportional to the amount of glucose in the sample positioned between the electrodes, the current generated would be proportional to the glucose content of the sample. A mediator, such as ferricyanide is a compound that exchanges electrons between a redox enzyme such as glucose oxidase and an electrode. In a different type of glucose test strip, the enzyme glucose dehydrogenase using a pyrroloquinoline quinone (PQQ) co-factor can be used instead of glucose oxidase. As the concentration of glucose increases, the amount of reduced mediator that is formed also increases, hence, there is a direct relationship between the glucose concentration and the current resulting from the re-oxidation of reduced mediator. In particular, the transfer of electrons across the electrical interface results in a flow of current (2 moles of electrons for every mole of glucose that is oxidized). The current resulting from the introduction of glucose may, therefore, be referred to as an analyte current or more particularly as a glucose current.

Since monitoring of blood glucose levels is an important tool in managing diseases such as diabetes, test meters, using the principles set forth above, have become popular. The glucose current generated during a test is recorded by the test meter and converted into a glucose concentration reading using a preset algorithm that relates current to glucose concentration via a simple mathematical formula. In general, the test meters work in conjunction with a disposable test strip that includes a sample reaction chamber containing electrodes and a reagent. In use, the user deposits a small sample of blood in the sample reaction chamber which is analyzed by the test meter to provide the user with a blood sugar level.

In electrochemical terms, the function of the test meter is twofold. Firstly, it provides a polarizing test potential (e.g., 0.4 V) that polarizes the electrical interface and allows a cell current to flow between two working electrode surfaces. Secondly, the test meter may measure the cell current. The test meter may, therefore be considered to be a simple electrochemical system that operates in a two-electrode mode although, in practice, third and, even fourth electrodes may be used to facilitate the measurement of glucose and/or perform other functions in the test meter.

In most situations, the equations set forth above are considered to be a sufficient approximation of the chemical reaction taking place in the test strip such that a reasonably accurate representation of the glucose concentration is obtained. However, under certain circumstances and for certain purposes, it may be advantageous to improve the accuracy of the measurement, for example, where a portion of the current measured at the electrode results from the presence of other chemicals or compounds in the sample. Where such additional chemicals or compounds are present, they may be referred to as interferents and the resulting additional current may be referred to as an interferent current.

Examples of potential interferents (i.e., compounds found in physiological fluids such as blood that may generate an interferent current in the presence of a test potential) include ascorbate, urate and acetaminophen (Tylenol™ or Paracetamol). A first mechanism for generating an interferent current in a test meter involves the oxidation of one or more interfering compounds by reduction of the mediator (e.g. ferricyanide). In turn, the resulting reduced mediator can then be oxidized at the working electrode. This first mechanism may also be referred to as an indirect interferent current. A second mechanism for generating an interferent current in a test meter involves the oxidation of one or more interferents at the working electrode. The second mechanism may be referred to as a direct interferent current. Thus, the measured cell current includes unwanted contributions from interferents.

A strategy that can be used to decrease the interferent effect is to use a second working electrode in conjunction with a first working electrode and reference electrode. If the second working electrode is bare, then the second working electrode can measure a direct interferent current. The first working electrode should have an enzyme and mediator for measuring a current which includes the summation of a glucose current, a direct interferent current, and an indirect interferent current. The direct interferent current measured at the second working electrode can be subtracted from the current at the first working electrode to reduce the effect of interferents.

Alternatively, or additionally, the second (or third) working electrode can be coated with a mediator (but not an enzyme) to allow the second working electrode to measure a current that includes a summation of the direct and indirect interferent current (but not glucose). In this case, the direct and indirect interferent current measured at the second working electrode can be subtracted from the current at the first working electrode to reduce the effect of interferents.

A disadvantage of using a second (or third) working electrode to compensate for the effects of interferents is that the second working electrode incrementally increases the sample reaction chamber volume and it is preferable that the sample reaction chamber be small so that users do not have to provide a large blood sample. A further disadvantage of using a second working electrode is that it increases manufacturing cost and complexity. Therefore, there is a need to develop methods for measuring glucose independent of interferents using only two electrodes.

SUMMARY

The present invention generally provides methods and apparatus for electrochemically determining an analyte concentration in a physiological sample. In one aspect, described herein, are methods of using a test strip in which a potential is applied and current is measured. Based on the current measurements, the methods allow analyte concentration to be found in a rapid manner while minimizing the effect of interferents.

In one embodiment, the method includes introducing a physiological sample into an electrochemical cell. A variety of electrochemical cells can be used, including for example a cell having first and second electrodes in a spaced apart relationship and a reagent. Once the sample is deposited, the method includes applying a first test potential having a first polarity to the reaction cell and measuring cell current as a function of time to obtain a first current transient. A second current transient is found by applying a second test potential having a second polarity to the cell, wherein the second polarity is opposite the first polarity, and measuring cell current as a function of time.

The first and second current transients are then analyzed to determine a first peak current value from the first current transient and a second peak current value from the second current transient. Based on the first and second peak current values, the effect of interferents in a sample can be determined.

In one embodiment, the effect of interferents is reduced by using the first and second peak current values to correct a current value. For example, a corrected current value can be determined by modifying a first current value derived from the second current transient. The resulting corrected current can represent the first current value, with the portion of the current resulting from interferents removed.

In one aspect, the contribution to the first current value from interferents is (at least partially) removed by multiplying the first current value and an interferent correction equation, wherein the interferent correction equation is $$\left\{ \frac{i_{pb} - 2i_{pa} + i_{ss}}{i_{pb} + i_{ss}} \right\}$$

The term $i_{pb}$ is the first peak current value, the term $i_{pa}$ is the second peak current value, and the term $i_{ss}$ is a steady-state current value.

The corrected current value can be used to determine analyte concentration. For example, the method can include the steps of calculating a second current value from the second current transient and a third current value from the first current transient. The analyte concentration can then be found from the equation $$[C] = \left(\frac{i_2}{i_3}\right)^P \times (a \times i_4 - Z)$$

where [C] is an analyte concentration, $i_4$ is a first corrected current value, $i_2$ is the second current value, $i_3$ is the third current value, and a, p, and Z are calibration factors.

In another embodiment disclosed herein, analyte concentration is determined based on the equation $$[C] = \left(\frac{i_{ss}}{i_{pp}}\right)^P \times \left(C_o\left\{\frac{i_{pb} - 2i_{pa} + i_{ss}}{i_{pb} + i_{ss}}\right\} - Z\right)$$

where [C] is an analyte concentration, $i_{pp}$ is a current value derived from the first current transient, $C_o$ is an estimated glucose concentration, Z is a calibration factor, $i_{pa}$ is the first peak current value, $i_{pb}$ is the second peak current value, and $i_{ss}$ is a steady state current value. In one alternative aspect, the term $i_{pp}$ is an average current over a short period of time near the end of the first current transient.

Another embodiment disclosed herein is a method for determining an analyte concentration in a physiological sample containing both an analyte and an interferent. The method includes introducing a physiological sample into an electrochemical cell and applying a first test potential having a first polarity to the reaction cell. The cell current value as a function of time is measured to obtain a first current transient. Next, an open-circuit potential time interval is allowed to elapse. After the open-circuit time potential elapses, a second current transient is measured by applying a second test potential having a second polarity.

Based upon the first and second current transients, first and second peak current values are found. The first peak current value is subtracted from the second peak current value to determine a corrected current that is proportional to the analyte concentration within the sample. The corrected current is used to calculate analyte concentration.

For example, analyte concentration can be found based upon the equation [C]=intercept+slope×($i_{pb}$, $i_{pa}$) where [C] is an analyte concentration, $i_{pa}$ is the first peak current value, $i_{pb}$ is the second peak current value, and slope and intercept are calibration factors. In another aspect, the equation is modified to account for reaction kinetics to provide the equation $$[C] = \left(\frac{i_2}{i_3}\right)^P \times \{\text{intercept} + \text{slope } x \ (i_{pb} - i_{pa})\}$$

where [C] is an analyte concentration, $i_{pa}$ is the first peak current value, $i_{pb}$ is the second peak current value, $i_2$ is a current value derived from the second current transient, $i_3$ is a current value derived from the first current transient, and slope and intercept are calibration factors.

In yet another embodiment, a method for determining a hemoglobin concentration in a physiological sample containing both an analyte and an interferent is disclosed. The method includes the step of introducing a physiological sample into an electrochemical cell, and applying a first test potential having a first polarity to the cell. The cell current value as a function of time is measured to obtain a first current transient. A second current transient is then found by applying a second test potential having a second polarity and measuring said cell current value as a function of time.

Based on the first current transient a first steady state current is determined and based on the second steady state current a second steady state current is determined. Subtracting the first steady state current value from the second steady state current value provides a current that is proportional to the hemoglobin concentration.

In one aspect, hemoglobin concentration is calculated based upon an equation $$[H] = \text{intercept} + \text{slope } x \ L\left\{\frac{i_{ssb} - i_{ssa}}{2FAD}\right\}$$

where [H] is an analyte concentration, $i_{ssa}$ is the steady state current from the first current transient, $i_{ssb}$ is the steady state current from the second current transient, slope and intercept are calibration factors, F is Faraday's constant, A is the area of the first electrode, D is the diffusion coefficient of the redox-active molecule, and L is the electrode spacing.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 2 is a bottom plan view of one embodiment of a test strip disclosed herein;

FIG. 3 is a side plan view of the test strip of FIG. 2;

FIG. 4A is a top plan view of the test strip of FIG. 3;

FIG. 4B is a partial side view of a proximal portion of the test strip of FIG. 4A;

DETAILED DESCRIPTION OF ILLUSTRATIVE EMBODIMENTS OF THE INVENTION

Figure 1A:
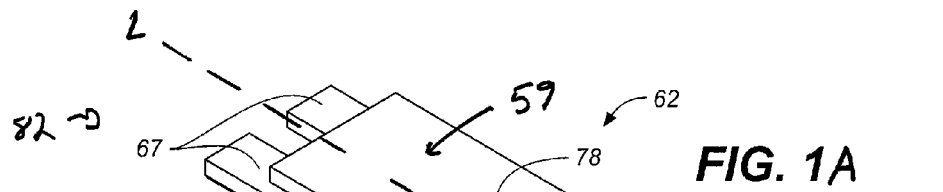
FIG. 1A illustrates a perspective view of an assembled test strip suitable for use in the methods disclosed herein.

The subject methods and devices are suited for use in the determination of a wide variety of analytes in a wide variety of samples, and are particularly suited for use in the determination of analytes in whole blood or derivatives thereof, where an analyte of particular interest is glucose. The subject invention provides methods for determining an analyte concentration value in a physiological sample in a rapid manner and with accurate results. Described herein are structures of exemplary test strip embodiments which can be used in measuring an analyte concentration value. Further, described herein are methods of using the test strip in which a current transient is measured and collected by a meter electrically connected to the test strip. Yet further described herein are algorithms which are used to process the current transient in a rapid manner and which output accurate analyte concentration values. In a further aspect, described herein, are methods for determining analyte concentration in a manner that reduces the influence of interferents.

The subject methods may be used, in principle, with any type of electrochemical cell having spaced apart first and second electrodes. To illustrate the invention, a particular embodiment using opposed electrodes is described herein. However, it is to be understood that the invention is equally applicable to cells with electrodes in other configurations, for example, cells with electrodes on the same plane can also be used. The only configuration limitation that need apply is that the electrodes must be placed such that the interferent current measurement is substantially free from contributions from electroactive species formed by reaction of the analyte (e.g. glucose). This is usually achieved by separating the electrodes by a sufficient distance such that electroactive species formed by reaction of the analyte do not have sufficient time to reach the electrode where the interferent current is being measured prior to or during the interferent current measurement.

Described below, and illustrated in FIGS. 1A through 4B, are various embodiments of one such device in the form of a test strip 62 including an elongate body 59 that extends along a longitudinal axis L from a proximal end 80 to a distal end 82 and having lateral edges 56, 58. Body 59 can include a proximal sample reaction chamber 61 that contains electrodes 164, 166 and a reagent 72. Test strip body 59 can further include distally positioned electrical contacts 63, 67 for electrically communicating with a test meter (not illustrated).

In one aspect, test strip 62 is formed from multiple layers including a first electrically conductive layer 66, a spacer 60, a second electrically conductive layer 64. First electrically conductive layer 66 and/or second electrically conductive layer 64 can be formed from a variety a conductive materials that are, in one embodiment, positioned on an insulating sheet (not shown). Spacer layer 60 can be formed from a variety of electrically insulating materials and can include, or be formed from, an adhesive. One skilled in the art will appreciate that while a three layer test strip is illustrated, additional electrically conductive or insulative layers could be used to form test strip body 59.

Figure 1B:
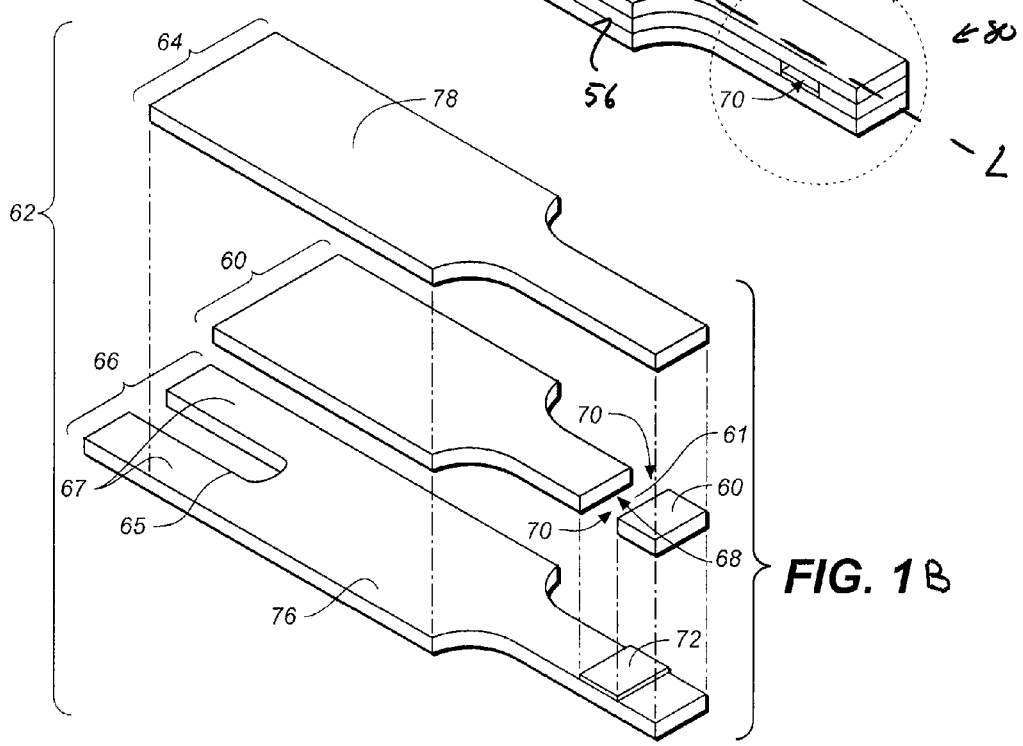
FIG. 1B illustrates an exploded perspective view of an unassembled test strip suitable for use in the methods disclosed herein.
Figure 1C:
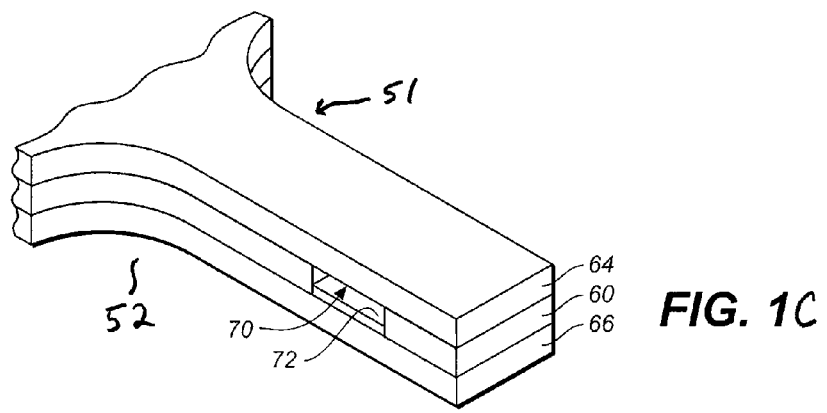
FIG. 1C illustrates an expanded perspective view of a proximal portion of the test strip suitable for use in the methods disclosed herein.

As illustrated in FIGS. 1A through 1C, proximal sample reaction chamber 61 can be defined by first electrically conductive layer 66, second electrically conductive layer 64, and spacer layer 60. As discussed in more detail below, reaction chamber 61 can also include a reagent 72 and first and second electrodes 166, 164. For example, a cutout area 68 in spacer 60 can expose a portion of second electrically conductive layer 64 and first electrically conductive layer 66, and thereby defines first electrode 166 and second electrode 164, respectively. Reagent 72 can be in the form of a layer positioned on first electrode 166.

In one embodiment, reaction chamber 61 is adapted for analyzing small volume samples. For example, sample reaction chamber 61 can have a volume ranging from about 0.1 microliters to about 5 microliters, preferably about 0.2 to about 3 microliters, and more preferably about 0.3 microliters to about 1 microliter. To accommodate a small sample volume, the electrodes are preferably closely spaced. For example, where spacer 60 define the distance between first electrode 166 and second electrode 164 the height of spacer 60 can be in the range of about 1 micron to about 500 microns, preferably between about 10 microns and about 400 microns, and more preferably between about 40 microns and about 200 microns.

To further assist with the reduction in the volume of reaction chamber 61 the longitudinal and/or lateral dimension of cutout area 68 and/or body 59 can be adjusted. For example, test strip body 59 can include cut-away portions 51, 52 such that the lateral width of reaction chamber 61 is smaller than the full width (widest width) of test strip body 59. Cut-away portions 51, 52 can also facilitate delivery of a sample to reaction chamber 61. For example, cut-away portion 51, 52 can have a shape corresponding to a portion of a finger of a user. When a user expresses a drop of blood with a finger stick, the cut-away portions 51, 52 can help the user align a sample positioned on his/her finger with a sample receiving port (e.g., openings 70) in the lateral edge 56, 58 of body 59. One skilled in the art will appreciate that while two cut-away portions are illustrated, test strip body 59 could include only a single cut-away portion or no cut-away portions.

As stated above, the proximal portion of test strip body 59 can include at least one sample delivery port for delivery of a sample to reaction chamber 61. For example, cutout area 68 can extend transversely to the lateral edges 56, 58 of test strip body 59 to provide two openings 70 for the delivering of physiological fluid to sample reaction chamber 61. Where two openings 70 are present one can act as a sample receiving port for delivery of a fluid sample while the other can act as a vent. One skilled in the art will appreciate that sample can be delivered to sample reaction chamber 61 using alternative structures including sample receiving ports and/or vents positioned at different locations in test strip body 59, such as, for example, sample receiving ports and/or vents positioned in first and/or second electrically conductive layers 66, 64.

In one embodiment, test strip 62 is adapted to draw sample into reaction chamber 61 via capillary action. For example, the dimensions and surface characteristics of reaction chamber 61 and openings 70 can be adapted to produce a capillary force when a liquid sample (e.g., whole blood) is brought into contact with one of openings 70. One skilled in the art will appreciate that reaction chamber 61 can include additional structures to assist with/create capillary forces such as, for example, beads, a porous membrane, and/or other fillers.

As mentioned above, a reagent, such as reagent 72, can be disposed within reaction chamber 61. The composition of reagent 72 can vary depending on the intended analyte and the expected form of the sample. In one aspect, reagent 72 includes at least a mediator and an enzyme and is deposited onto first electrode 166. Example of suitable mediators include ferricyanide, ferrocene, ferrocene derivatives, osmium bipyridyl complexes, and quinone derivatives. Examples of suitable enzymes include glucose oxidase, glucose dehydrogenase (GDH) based on pyrroloquinoline quinone (PQQ) co-factor, and GDH based on nicotinamide adenine dinucleotide co-factor. One exemplary reagent formulation, which would be suitable for making reagent layer 72, is described in pending U.S. application Ser. No. 10/242,951, entitled, Method of Manufacturing a Sterilized and Calibrated Biosensor-Based Medical Device, published as U.S. Published Patent Application No. 2004/0120848, which is hereby incorporated by reference in its entirety.

Distal to the proximal sample chamber 61, body 59 can include connection tracks that electrically connect first and second electrodes 166, 164 with distal electrical contacts 63, 67. In one aspect, first electrically conductive layer 66 includes a first connection track 76 that electrically connects first electrode 166 with a first electrical contact 67. Similarly, second electrically conductive layer 64 can include a second connection track 78 that connects the second electrode 164 with a second electrical contact 63 (FIG. 2).

First and second electrically conductive layers can also define first and second electrical contacts 67, 63 that facilitate electrical contact of test strip 62 with a test meter. In one embodiment, a portion of first electrically conductive layer 66 extends distally from the distal end of spacer layer 60 and second electrically conductive layer 64 to define first electrical contact 67. Second electrical contact can be defined by a U-shaped notch 65 in the first electrically conductive layer 66 which exposes a portion of second electrically conductive layer 64. One skilled in the art will appreciate that test strip 62 can include a variety of alternative electrical contact configurations for electrically connecting to a test meter. For example, U.S. Pat. No. 6,379,513 discloses electrochemical cell connection structures, and is hereby incorporated by reference in its entirety.

Figure 5:
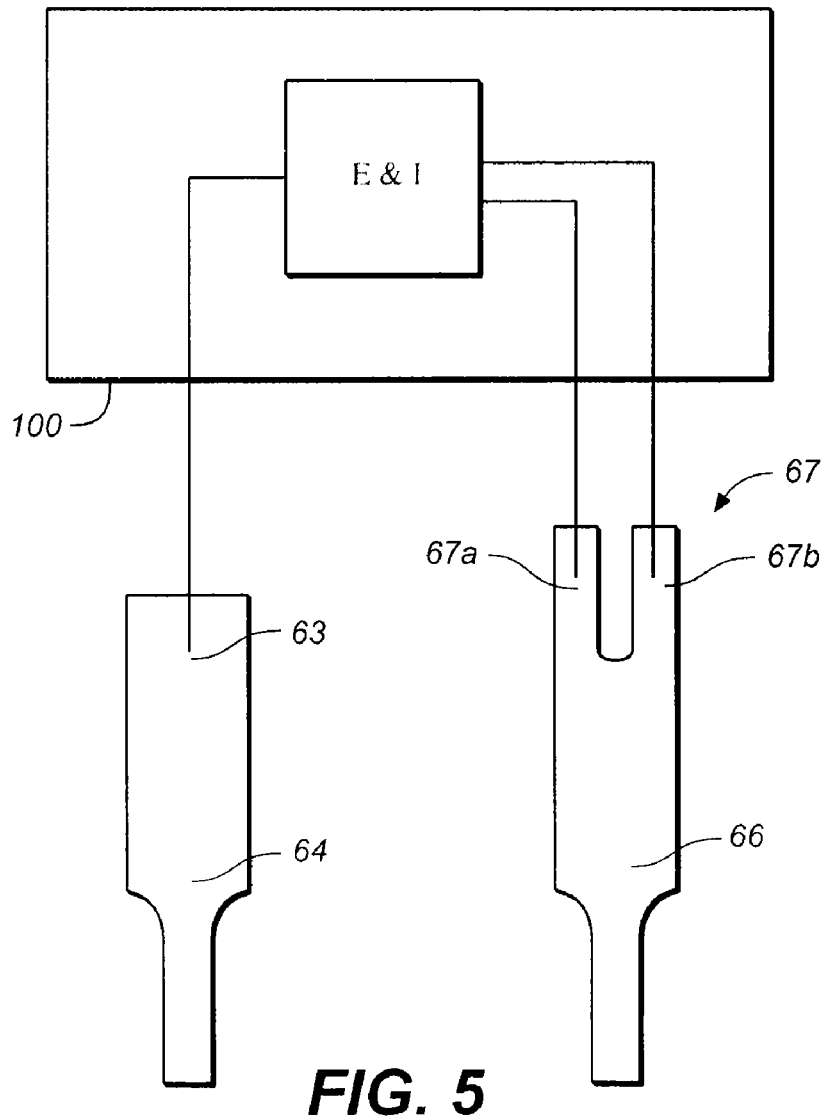
FIG. 5 is a simplified schematic showing a test meter electrically interfacing with portions of a test strip disclosed herein.

FIG. 5 provides a simplified schematic showing a test meter 100 interfacing with first electrical contact 67 and second electrical contact 63, which are in electrical communication with first electrode 166 and second electrode 164, respectively, of test strip 62. Test meter 100 is adapted to electrically connect to first electrode 166 and second electrode 164, via first electrical contact 67 and second electrical contact 63, respectively (as shown in FIGS. 2 and 5). In one aspect, test meter 100 contacts second electrical contact 63 through U-shaped notch 65.

As illustrated in FIG. 5, electrical contact 67 can include two prongs denoted as 67a and 67b. In one exemplary embodiment, test meter 100 separately connects to prongs 67a and 67b, such that when test meter 100 interfaces with test strip 62 a circuit is completed. Test meter 100 can measure the resistance or electrical continuity between prongs 67a and 67b to determine whether test strip 62 is electrically connected to test meter 100. One skilled in the art will appreciate that test meter 100 can use a variety of alternative sensors and/or and circuits to determine when test strip 62 is properly positioned with respect to test meter 100.

Test meter 100 can also be adapted to detect the presence of fluid within reaction chamber 61. For example, once test meter 100 recognizes that strip 62 has been inserted, test meter 100 can apply a constant current (e.g., a current of 1 microampere) between first electrode 166 and second electrode 164. Because reaction chamber 61 is initially dry, test meter 100 can apply a maximum voltage in an attempt to achieve the desired current flow. However, once a user doses a physiological sample onto inlet 70, this cause sample reaction chamber 61 fill. When the physiological sample bridges the gap between first electrode 166 and second electrode 164, test meter 100 will measure a decrease in measured voltage (e.g., as described in U.S. Pat. No. 6,193,873) which is below a predetermined threshold.

In some cases, recognizing that physiological fluid was applied does not necessarily indicate that sample reaction chamber 61 is completely filled, but may only confirm a presence of some physiological fluid in sample reaction chamber 61. Once test meter 100 determines that physiological fluid has been applied to test strip 62, a short, but finite amount of time can be allowed to elapse so that the physiological fluid completely fills sample reaction chamber 61.

Figure 6:
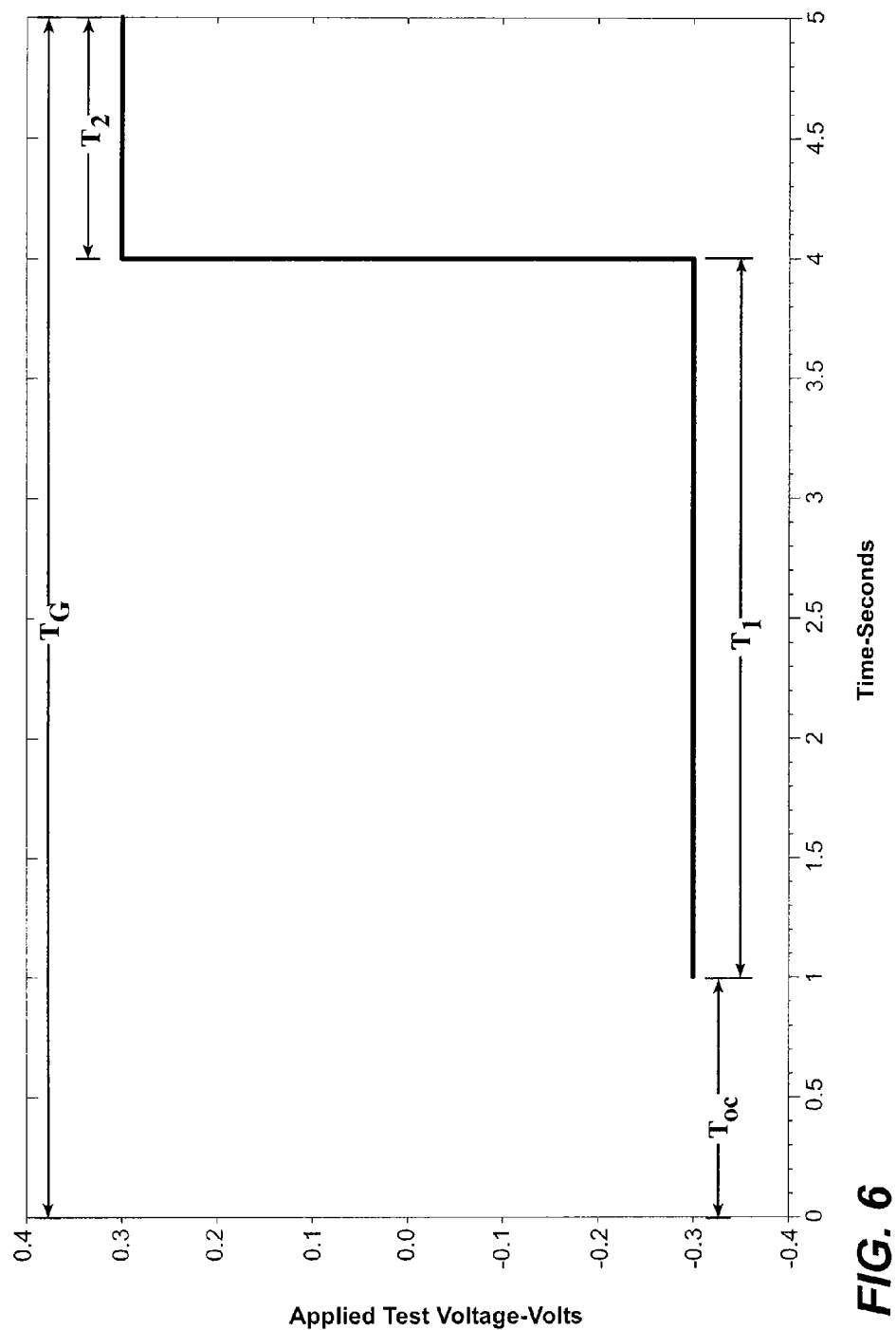
FIG. 6 shows an example of a potential waveform in which a test meter applies an open-circuit potential and a plurality of test potentials for prescribed time intervals.

Once a physiological sample has been dosed onto test strip 62, test meter 100 may perform a glucose test by applying an open-circuit potential and a plurality of test potentials for prescribed periods of time. For example, a glucose test may be performed over a glucose test time interval $T_G$ which may sequentially include an open-circuit time interval $T_{OC}$, a first potential time interval $T_1$, and a second test potential time interval T$_2$. FIG. 6 provides a graphical representation of one exemplary test having three time intervals.

In the following embodiment of this invention, a series of time intervals will be described collectively representing a glucose test time interval T$_G$ of 5 seconds. However it should be appreciated that the glucose time interval can vary, including for example, time intervals of more or less than 5 seconds. In one aspect, glucose test time intervals T$_G$ can range from about 1 second to 10 seconds, preferably in the range of about 2 to 8 seconds, and more preferably in the range of about 3 to 6 seconds. A glucose test can being with an open-circuit time interval T$_{OC}$ to allow sample reaction chamber 61 to fill. Open-circuit time interval T$_{OC}$, can be varied depending on the nature of the sample (e.g., viscosity, composition, etc.), the dimensions and physical characteristics of the sample reaction chamber, and/or variations in the filling method (e.g., the strength of the capillary action). For example, when the ambient temperature is cold (e.g., about 5° C.) and/or when a blood sample may be viscous because of a high hematocrit (e.g., >60% hematocrit) extra open-circuit time might be required. In one embodiment of this invention, open-circuit time interval T$_{OC}$ may be in the range of about 0.1 seconds to about 2 seconds and preferably between about 0.3 seconds to about 1.5 seconds, and more preferably between about 0.5 to about 1 second.

Once open-circuit time interval T$_{OC}$ has elapsed, test meter 100 can apply a first test potential E$_1$ between first electrode 166 and second electrode 164 for a first test potential time interval T$_1$. After first test potential time interval T$_1$ has elapsed, test meter 100 can apply a second test potential E$_2$ between first electrode 166 and second electrode 164 for a second test potential time interval T$_2$. During T$_1$ and T$_2$, test meter 100 can measure cell current as a function of time, herein called a time current transient or a current transient and referred to as i$_a$(t), during first test potential time interval T$_1$, and as i$_b$(t) during the second test potential time interval T$_2$.

In one embodiment, first test potential E$_1$ has a first polarity and second test potential E$_2$ has a second polarity, and the first polarity is opposite the second polarity. In addition, first test potential E$_1$ can be sufficiently negative in magnitude with respect to second electrode 164 such that second electrode 164 functions as a working electrode in which a limiting oxidation current is measured. Oxidizable species are thus locally depleted at the working electrode surface such that the measured oxidation current is proportional to the flux of oxidizable species diffusing from the bulk solution towards the working electrode surface. The term "bulk solution" refers to a portion of the solution sufficiently far away from the working electrode where the oxidizable species was not located within the depletion zone. Similarly, second test potential E$_2$ can be sufficiently positive in magnitude with respect to second electrode 164 such that first electrode 166 functions as a working electrode in which a limiting oxidation current is measured. In one embodiment, first test potential E$_1$ and second test potential E$_2$ may range from about –0.6 Volts to about +0.6 Volts. Where first test potential E$_1$ is negative, reagent 72 can be disposed on first electrode 166.

FIG. 6 illustrates one exemplary glucose test time interval T$_G$ with first test potential E$_1$ of –0.3 Volts and second test potential E$_2$ may be +0.3 Volts. The first test potential time interval T$_1$ was 3 seconds and second test potential time interval T$_2$ was 1 second. Second test potential E$_2$ is applied immediately following the application of the first test potential E$_1$.

Figure 7:
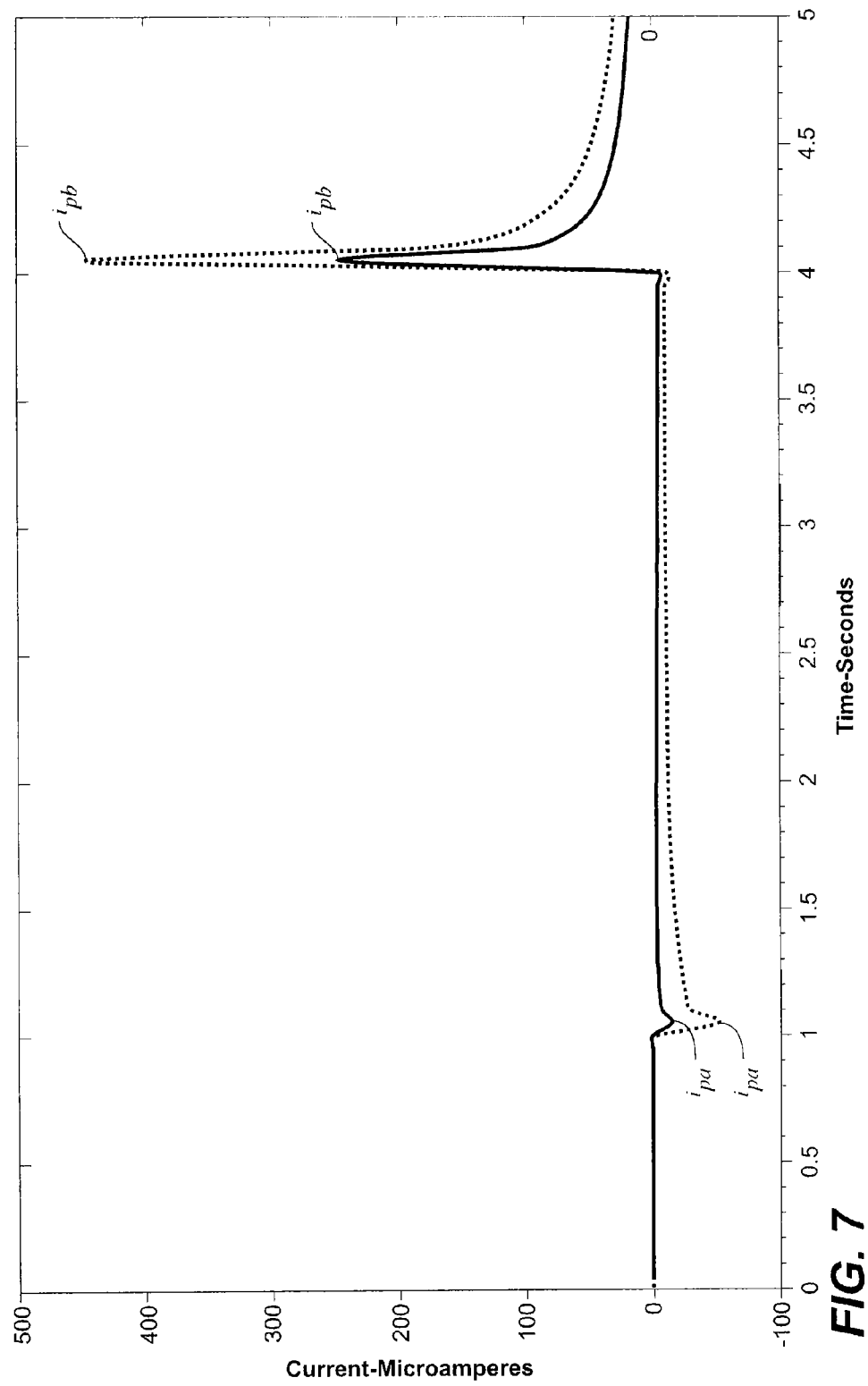
FIG. 7 shows a first and second current transient generated testing a physiological sample containing 62 mg/dL glucose concentration without added interferents (solid line) and with a 20 mg/dL ascorbate concentration (dotted line)
Figure 8:
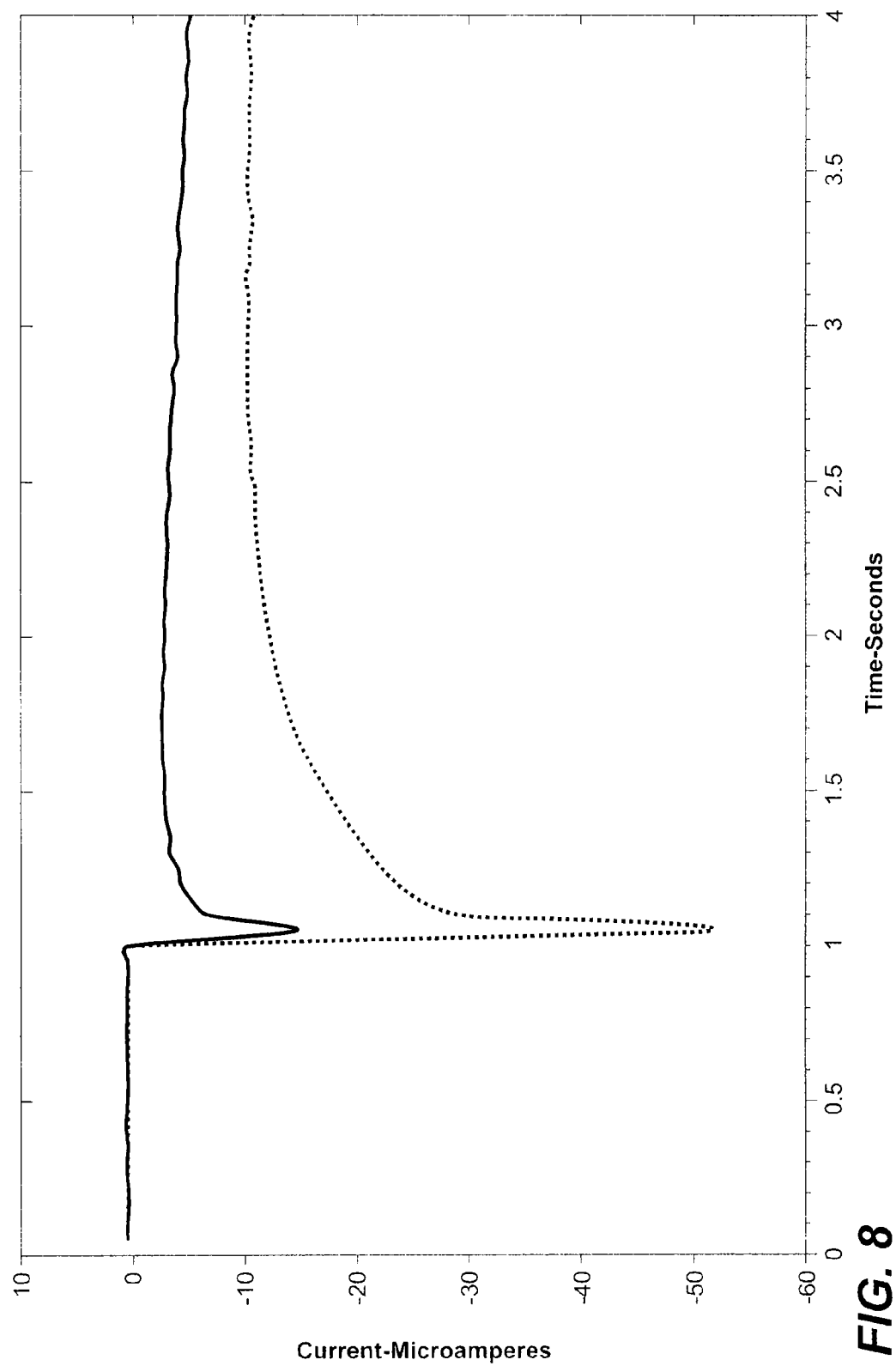
FIG. 8 is an expanded view of FIG. 7 showing a first current transient.

FIG. 7 shows first and second current transients generated based on the glucose test time interval T$_G$ of FIG. 6 for a physiological sample containing 62 mg/dL glucose concentration without added interferents (solid line) and with a 20 mg/dL ascorbate concentration (dotted line). FIG. 8 shows an expanded view of a first current transient in FIG. 7.

Assuming that a test strip has an opposing faced or facing arrangement as shown in FIGS. 1A to 4B, a glucose concentration can be calculated using a first glucose algorithm as shown in Equation (Eq.) 1.

$$[G] = \left(\frac{i_2}{i_3}\right)^p \times (a \times i_1 - Z) \quad \text{Eq. 1}$$

In Eq. 1, [G] is the glucose concentration, i$_1$ is a first current value, i$_2$ is a second current value, and i$_3$ is a third current value, and the terms p, Z, and a are empirically derived calibration constants. A derivation of Eq. 1 can be found in a pending U.S. application Ser. No. 11/240,797 which was filed on Sep. 30, 2005 and entitled "Method and Apparatus for Rapid Electrochemical Analysis," which is hereby incorporated by reference in its entirety.

First current value i$_1$ and second current value i$_2$ can be calculated from the second current transient and third current value i$_3$ is calculated from the first current transient. One skilled in the art will appreciate that names "first," "second," and "third" are chosen for convenience and do not necessarily reflect the order in which the current values are calculated. All current values (e.g. i$_1$, i$_2$, and i$_3$) stated in Eq. 1 and in subsequent equations can use the absolute value of the current.

First current value i$_1$ and second current value i$_2$ can be, in one aspect, an integral of current values over a time interval of the second current transient, a summation of current values over a time interval of the second current transient, or an average or single current value of the second current transient multiplied by a time interval of the second current transient. Similarly, third current value i$_3$ may be, in one aspect, an integral of current values over a time interval of the first current transient, a summation of current values over a time interval of the first current transient, or an average or single current value of the first current transient multiplied by a time interval of the first current transient. For the summation of current values, a range of consecutive current measurement can be summed together from only two current values or to all of the current values.

In another embodiment, first current value i$_1$, second current value i$_2$, and third current value i$_3$ can be replaced with a coulombic value. Instead of measuring a current, the passed charge can be measured. The total charge passed provides the same information as integrating a current transient. For example, the charge passed can be measured over a predetermined time interval and used for the first, second, and/or third current value.

In one embodiment of a method disclosed herein, glucose reaction kinetics are accounted for by using current values (e.g. i$_1$, i$_2$, and/or i$_3$). The result is less dependent on hematocrit concentration and temperature, and improved accuracy and precision in the determination of glucose concentration can be achieved.

In one aspect, reagent layer 72 is disposed on first electrode 166 and thus generally remains proximate to first electrode 166 after its dissolution with physiological sample. This results, at least initially, in a major proportion of reduced mediator being proximate to first electrode 166. After a certain period of time has passed, reduced mediator, generated in reagent layer 72 by the reaction of glucose, will passively diffuse away from first electrode 166. During this process, the magnitude of the mediator concentration between first electrode 166 and second electrode 164 forms a gradient in which the reduced mediator concentration is higher at first electrode 166 and lower at second electrode 164. A larger concentration of reduced mediator at first electrode 166 will cause the magnitude of the gradient to become steeper. The magnitude of the first current transient is proportional to the magnitude of this gradient. Therefore, the amount of reduced mediator generated by reagent layer 72 drives the diffusion of reduced mediator to second electrode 164. The rate of change of the current measured at the electrodes is thus indicative of the rate of change of the reduced mediator concentration at reagent layer 72 and also of the glucose reaction kinetics (i.e., the reaction rate of glucose which generates reduced mediator).

The glucose reaction kinetics depends on several factors that include the electrode spacing (as it relates to the maximum distance the glucose has to diffuse to get to the reagent layer 72), viscosity of the physiological sample, hematocrit concentration, and the temperature.

A viscosity increase in the physiological sample can occur with increases in hematocrit, protein, lipid content, or combinations thereof. Hematocrit refers to the proportion of red cells in a blood sample. Typically, a higher proportion of red cells causes blood to be more viscous and results in a larger proportion of the total glucose to be inside the red cells. In order for glucose inside the red cells to react with reagent layer 72, the glucose must transport across the red cell membrane. Under certain conditions, this transport may be relatively slow so as to limit the glucose reaction kinetics. Therefore, higher hematocrit slows the glucose reaction kinetics. Viscosity generally slows down the general diffusion process within sample reaction chamber 61. A higher temperature generally increases the reaction rate of glucose with reagent layer 72 within sample reaction chamber 61 as it speeds up the transport processes involved.

The current values ($i_1$, $i_2$, and/or $i_3$), and particularly a ratio of current values, can be used to correct for the variations in glucose reaction kinetics. For example, the magnitude of the second current transient will generally be larger than the absolute magnitude of the first current transient. Thus, the ratio $i_2/i_3$ will generally be greater than unity, while the glucose reaction is underway within sample reaction chamber 61 and would become unity when the glucose reaction is complete. The departure of the ratio $i_2/i_3$ from unity will therefore be a factor in indicating the degree of reaction completion. Relatively large values of $i_2/i_3$ will indicate that the glucose reaction is far from completion whereas $i_2/i_3$ values close to unity will indicate that the glucose reaction is nearly complete. Therefore, the ratio $i_2/i_3$ generally provides information on the progress of the glucose reaction and can be used to eliminate the effect of hematocrit, viscosity, and temperature on the measurement of glucose concentration.

To further refine the calculations, one or more calibration factors can be used. For example, as shown in Eq. 1, the ratio $i_2/i_3$ is set to the exponential p in which p is a calibration factor that can be used for a particular lot of test strip. The use of exponent p was found through empirical means to improve the accuracy and enable rapid test times. In one embodiment of the invention, p may range from about 0.2 to about 4, and preferably between about 0.1 to about 1.

As shown in Eq. 1, a calibration factor a can be used to account for possible variations in cutout area 68 and height of spacer 60. Variations in cutout area 68 can cause a proportional shift in the magnitude of the measured current. Under certain circumstances, manufacturing processes can cause the electrode area to vary from one lot of test strips to another lot of test strips. Similarly, the height of spacer 60 also can vary between lots. Variations in the height of spacer 60 have a proportional impact on the test current. For example, an increase in the height of spacer 60 leads to a decrease in the test current. Calculating a calibration factor a for each lot of test strips helps to compensate for variations in electrode area and the height of spacer 60. The term a can be calculated during the calibration process of a test strip lot.

In one embodiment, as shown in Eq. 1, a calibration factor Z is used to account for variations in the background. A presence of an oxidizable species within reagent layer 72 before adding physiological fluid to test strip 62 may contribute to a background signal. For example, if reagent layer 72 were to contain a small amount of ferrocyanide (e.g., reduced mediator) before physiological fluid was added to the test strip, then there would be an increase in the measured test current which would not be ascribed to the glucose concentration. Because this would cause a constant bias in the overall measured test current for a particular lot of test strips, this bias can be corrected for using the calibration factor Z. Similar to the terms p and a, Z can also be calculated during the calibration process.

While the method disclosed herein is described with the use of calibration factors, p, a, and Z, one skilled in the art will appreciate that their use is not required. For example, in one embodiment, glucose concentration could be calculated without p, a, and/or Z (in Eq. 1 p and/or a could be set equal to one and Z could be set equal to zero).

The selection of the time intervals in which $i_1$, $i_2$, and $i_3$ are calculated can be determined with a training algorithm for a particular type of test strip (i.e., determined empirically). During the training algorithm, several test strips would be tested over a range of conditions that a user may encounter during testing. Such conditions may include a glucose concentration range from 20 mg/dL to 600 mg/dL, a hematocrit range from 0% to 70%, a temperature range from 5° C. to 45° C., humidity range from 5% relative humidity (5% RH) to 95% RH, and endogenous and exogenous interferents. Examples of endogenous and exogenous interferents and their physiological concentration ranges can be found in a publication entitled "National Committee for Clinical Laboratory Standards: Interferent Testing in Clinical Chemistry; proposed guideline EP7-P." Wayne, P A.: NCCLS, 1986, which is incorporated by reference herein. Using standard minimization or error techniques, an optimized selection of time intervals or $i_1$, $i_2$, and $i_3$ was defined such that the calculated glucose concentration using Eq. 1 was accurate (e.g., within ±10% of a reference measurement) and precise (e.g., strip-to-strip variation of about 2% or less at 1σ). One skilled in the art will appreciate, the chosen time interval for first current value, second current value, and third current value can thus be the same or different, and in one embodiment, only two current values are calculated. For example, second current value $i_2$ may be defined to be the same as first current value $i_1$.

After the time interval of $i_1$, $i_2$, and $i_3$ are chosen, the strip lot can be calibrated. Exemplary methods for calibrating strip lots are described in U.S. Pat. No. 6,780,6465 which is hereby incorporated by reference in its entirety. More particularly, the calibration factors a, p, and/or Z can be calculated for a particular lot of test strips. Typically, a range of glucose concentrations in blood from multiple donors are tested using the glucose test strips and also in a reference instrument known to be accurate and precise. The error between the results from the test strips of the present invention and the reference method is minimized by finding the optimal combination of a, p, and/or Z. In one embodiment, the calibration information can be transmitted to and/or stored in a test meter 100 before using a test strip from the test strip lot.

Described are further methods of calculating analyte concentration which can account for the presence of interferents in a sample. For example, certain diseases such as gout will cause a person's urate concentration to be elevated which may affect the accuracy of a glucose measurement. Urate is a potential interferent for many electrochemical measurements because it can be easily oxidized at a working electrode surface and/or by an oxidized mediator. In an embodiment of this invention. Eq. 1 was modified to increase the accuracy of the glucose measurement in the presence of interferents such as urate. In order to develop a modified algorithm, a mathematical relationship was found based on the oxidation of interferents during the first current transient and the second current transient.

If we assume that the overall concentration of reduced mediator does not change within sample reaction chamber 61 during the glucose test time interval $T_G$, a magnitude of current for the first current transient can be described as a function of time by Eq. 2.

$$i_a(t) = i_{ss} \left\{ 1 + 2 \sum_{n=1}^{x} \exp\left(\frac{-4\pi^2 n^2 Dt}{L^2}\right) \right\} \quad \text{Eq. 2}$$

The term $i_{ss}$ is the steady-state current following the application of first test potential $E_1$, D is the diffusion coefficient of the mediator, L is the thickness of spacer 60. It should be noted that in Eq. 2, t refers to the time elapsed after first test potential $E_1$ was applied. For example, to be consistent with FIG. 7, the t value used in Eq. 2 should have 1 second subtracted from the actual time. A magnitude of current for the second current transient can be described as a function of time by Eq. 3.

$$i_b(t) = i_{ss} \left\{ 1 + 4 \sum_{n=1}^{x} \exp\left(\frac{-4\pi^2 n^2 Dt}{L^2}\right) \right\} \quad \text{Eq. 3}$$

There is a factor of two difference for the exponential term in Eq. 3 as compared to the exponential term in Eq. 2 because the second current transient is generated from the second test potential $E_2$, which was opposite in polarity to the first test potential $E_1$, and was applied immediately after the first test potential $E_1$. It should be noted that in Eq. 3, t refers to the time elapsed after second test potential $E_2$ was applied. For example, to be consistent with FIG. 7, the t value used in Eq. 3 should have 4 seconds subtracted from the actual time. During a first test potential $E_1$ of –0.3V, interferent is oxidized at second electrode 164 and in turn generates reduced mediator at the first electrode 166. It is this accumulation of reduced mediator at the first electrode 166 which causes the initial current at the second test potential $E_2$ to be twice as big for the exponential term.

Figure 9:
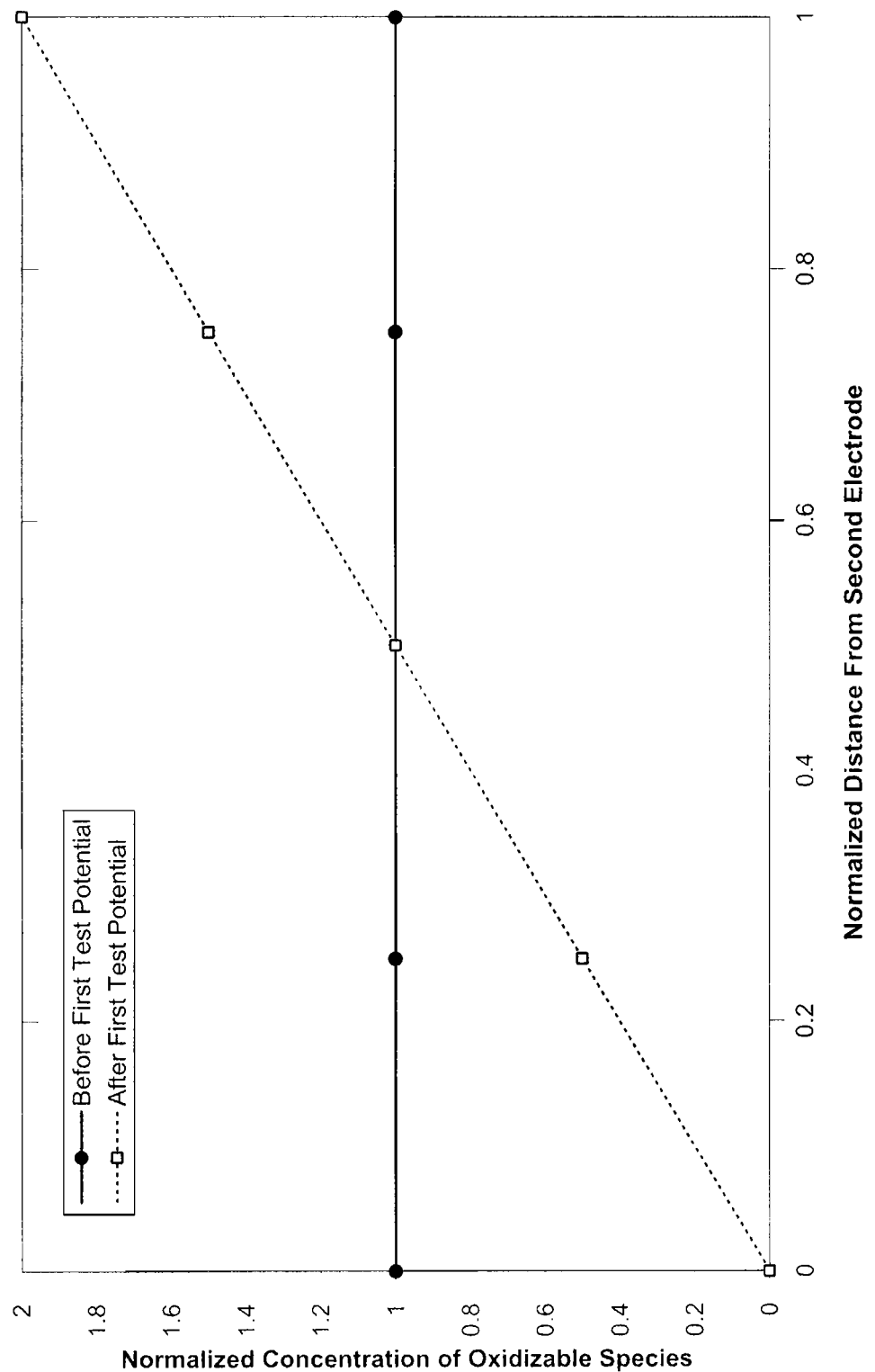
FIG. 9 is a graphical representation of a concentration gradient of reduced mediator within a sample reaction chamber.

FIG. 9 shows a graphical representation of a concentration gradient within sample reaction chamber 61 which may be used to explain the factor of two difference for the exponential term in Eq. 3 as compared to the exponential term in Eq. 2. If we assume that a concentration of reduced mediator within sample reaction chamber 61 does not change during the glucose test time interval $T_G$, the concentration of oxidizable species should be uniform throughout sample reaction chamber 61 before first test potential $E_1$ is applied to test strip 62. The circles in FIG. 9 indicate that the normalized concentration of oxidizable species was uniform by showing the concentration as unity. This initial concentration may also be referred to as the bulk concentration. Once first test potential $E_1$ is applied, the normalized concentration of oxidizable species at second electrode 164 immediately becomes depleted causing the concentration to be zero. Note that the surface of second electrode 164 is represented as zero on the X-axis and that the normalized distance from second electrode 164 to first electrode 166 is represented as one on the X-axis, according to FIG. 9.

After applying first test potential $E_1$, the normalized concentration of oxidizable species becomes twice as large as the bulk concentration at first electrode 166, which in this case is two. In addition, a linear concentration gradient forms within sample reaction chamber 61 as indicated by the squares, according to FIG. 9, where the normalized concentration of oxidizable species is highest at first electrode 166 and lowest at second electrode 164. Because there is a conservation of charge within sample reaction chamber 61, every oxidizable species consumed at second electrode 164 must result in an oxidizable species generated at first electrode 166. Thus, the normalized concentration of oxidizable species at first electrode 166 is two after the application of first test potential $E_1$.

Upon applying second test potential E2, the current a short time later will be twice as high as the current at the same time after the application of E1 less the steady state current. The reason for the factor of two is because the initial concentration of oxidizable species at first electrode 166 will be twice the bulk concentration. In contrast, the initial normalized concentration of oxidized species at second electrode 164 before applying first test potential $E_1$ was only half as much, which in this case was the bulk concentration. The reason for the subtraction of the steady state current is that there is a gradient of oxidizable species between the two electrodes which causes flow of electrons decay from the first electrode 166.

FIG. 7 shows that there is a peak current for first test potential time interval $T_1$ which is denoted as $i_{pa}$ and a peak current for second test potential time interval $T_2$ which is denoted as $i_{pb}$. If both first peak current $i_{pa}$ and second peak current $i_{pb}$ were measured at the same short time after the application of first test potential $E_1$ and second test potential $E_2$ respectively, for example 0.1 seconds, Eq. 2 can be subtracted from Eq. 3 to yield Eq. 4.

$$i_{pb} - 2i_{pa} = -i_{ss} \quad \text{Eq. 4}$$

It should be noted that Eq. 2 was multiplied by two so as to allow the summation terms to cancel out. Eq. 4 describes a relationship between the first current transient and second current transient when test strip 62 is tested with a sample containing an interferent and no glucose. Because there is no glucose in the sample, reagent layer 72 does not generate reduced mediator during the glucose test time interval $T_G$. Therefore, the first and second current transients would both reflect only the oxidation of interferents. It is apparent from the above discussion that the relationship between the first and second peak currents and the steady state current can be derived by recourse to the fundamental electrochemical equations, or by verbal/graphical heuristic arguments. Both approaches can lead to Eq. 4.

Open-circuit time interval $T_{OC}$ may be used to improve the sharpness of first peak current value $i_{pa}$ where the peak forms immediately after the application of first test potential $E_1$. A nominal open-circuit time interval $T_{OC}$ allows sample reaction chamber to completely fill. In addition, a nominal open-circuit time interval $T_{OC}$ also allows reagent layer 72 to dissolve which enables oxidized mediator to be reduced by first electrode 166 so that a limiting oxidation current may be measured at second electrode 164.

The magnitude of the first and second current transients have a more complicated relationship if reagent layer 72 generates reduced mediator during glucose test time interval $T_G$. At an early time scale regime of around 1.1 seconds, it is assumed that reagent layer 72 does not generate a significant amount of reduced mediator because of the glucose reaction. Further, it is assumed that the reduced mediator which is generated will mostly remain near first electrode 166, where reagent layer 72 was initially deposited, and not significantly diffuse to second electrode 164. Therefore, the magnitude of the $i_{pa}$ is predominantly ascribed to interferent oxidation at second electrode 164 which is a direct interferent current.

At a later time scale regime of around 4.1 seconds, reagent layer 72 does generate a significant amount of reduced mediator at first electrode 166 in the presence of glucose because of the glucose reaction. A significant amount of reduced mediator can also be generated because of a possible oxidation of an interferent with the oxidized mediator. As mentioned earlier, interferent that reduces oxidized mediator contributes to a current which may be referred to as an indirect current. In addition, interferents can also be oxidized directly at first electrode 164 which may be referred to as a direct current. For the situation in which the mediator can be oxidized at the working electrode, it may be assumed that the sum of the direct oxidation and indirect oxidation is approximately equal to a direct oxidation current that would have been measured if there was no oxidized mediator disposed on the working electrode. In summary, the magnitude of the $i_{pb}$ is ascribed to both indirect and direct interferent oxidation, and the glucose reaction at second electrode 164. Because it has been determined that $i_{pa}$ is controlled mainly by interferents, $i_{pb}$ can be used with $i_{pa}$ together to determine a correction factor. For example, as shown below $i_{pb}$ can be used with $i_{pa}$ in a mathematical function to determine a corrected current which is proportional to glucose and less sensitive to interferents.

Eq. 5 was empirically derived to calculate a current $i_4$ which is proportional to glucose and has a relative fraction of current removed that is ascribed to interferents.

$$i_4 = i_2 \left\{ \frac{i_{pb} - 2i_{pa} + i_{ss}}{i_{pb} = i_{ss}} \right\} \qquad \text{Eq. 5}$$

The term $i_{ss}$ was added to both the numerator and denominator to allow the numerator to approach zero when no glucose is present. The term $i_{ss}$ may be estimated using Equation 5B, for currents at times greater than a minimum time, where a suitable minimum time can be estimated from Equation 5C.

$$i(t) = i_{ss}\left\{1 + 4\exp\left(\frac{-4\pi^2 Dt}{L^2}\right)\right\} \qquad \text{Eq. 5B}$$

$$t_{min} = \frac{-L^2 \ln 0.01}{12\pi^2 D} \qquad \text{Eq. 5C}$$

in which, $i_{ss}$ is the steady-state current following application of the second electric potential; i is the measured current which is a function of time; D is the diffusion coefficient of the redox-active molecule, where this coefficient may be determined from Fick's first law, i.e. $J(x,t)=-D\, dC(x,t)/dx$; L is the spacer thickness; and t is the time for the application of the second electric potential where t=0 for the beginning of the second time interval.

Eq. 1 can be modified by replacing the term $i_1$ for the term $i_4$ to give a second glucose algorithm which is shown in Eq. 6.

$$[G] = \left(\frac{i_2}{i_3}\right)^p \times (\alpha \times i_4 - Z) \qquad \text{Eq. 6}$$

Thus, Eq. 6 will enable accurate measurements of glucose in the presence of interferents using only two electrodes.

In another embodiment of the present invention, a glucose algorithm as shown in Eq. 7 can be used to measure glucose in the presence of interferents. In Eq. 7 initial concentration $C_o$ is multiplied by a correction factor. The product is proportional to the reacted glucose concentration plus background reduced mediator. As such, the term Z is subtracted and the result is multiply by the (iss/ipp)^p to get to the measure of the total glucose in the sample.

$$[G] = \left(\frac{i_{ss}}{i_{pp}}\right)^p \times \left(C_o \left\{\frac{i_{pb} - 2i_{pa} + i_{ss}}{i_{pb} + i_{ss}}\right\} - Z\right) \qquad \text{Eq. 7}$$

The term $i_{pp}$ is a current value derived from the first current transient. In one aspect, $i_{pp}$ is an average current over a short period of time near the end of the first current transient. For example, the average current can be found between 3.8 and 4.0 seconds. $C_o$ is an estimated glucose concentration which is defined by Eq. 8, $$C_o = \frac{i_{ss} L}{2 FAD} \qquad \text{Eq. 8}$$

in which F is a Faraday's constant, i.e. 96,485 Coulombs/mole, and A is the area of first electrode.

Certain interferents do not oxidize easily directly at an electrode surface. For example, acetaminophen may not oxidize easily at second electrode 164 where it is made of sputtered gold and first electrode is held at −0.3V. If it is not possible to measure a direct interferent current at second electrode 164, the relationship of $i_{pa}$ and $i_{pb}$ due to interferents will no longer follow Eq. 4 in the absence of glucose. In turn, Eq.'s 6 and Eq. 7 will not provide as accurate a measure of glucose in the presence of interferents. To remedy the problem of not measuring an interferent current at second electrode 164, a second reagent layer, which includes an oxidized mediator and is substantially free of enzyme, may be disposed on second electrode 164. An oxidized mediator such as, for example, ferricyanide may then easily oxidize acetaminophen allowing an indirect interferent current to be measured at second electrode 164. By allowing the oxidation of interferents to be measured at second electrode 164, this allows Eq. 6 and 7 to calculate accurate glucose concentrations in the presence of interferents.

In another embodiment to remedy this problem the oxidized mediator dried onto the first electrode can be in sufficient quantity and/or dried in such a way that a portion of the oxidized mediator is mixed into the bulk of the sample as it fills the cell while not allowing a significant amount of enzyme to mix into the bulk of the sample. This can be achieved for example by having sufficient oxidized mediator in the formulation and drying it slowly enough such that at least a portion of the oxidized mediator crystallizes substantially free of enzyme. The crystals can dissolve and mix into the sample to a greater extent than the enzyme, aided by ensuring that the mediator has a substantially smaller size compared to the enzyme. In this way potential interferents can be oxidized by the oxidized mediator to form reduced mediator which can be measured as part of the interferent current, obviating a second reagent layer.

In another embodiment, an open-circuit potential is introduced between the first test potential $E_1$ and the second test potential $E_2$. While this open-circuit potential is referred to herein as a "second" open-circuit, the use of the term "second" is used for convenience and does not require a "first" open-circuit potential. The second open-circuit potential allows the electrochemical gradient to decay back to the unperturbed state (i.e., the oxidized mediator that accumulated at first electrode 166 because of the application of first test potential $E_1$ may diffuse back into the bulk solution). Under these conditions, the interferent effect can be removed by subtracting the first current transient directly from the second current transient. As mentioned earlier, the initial current, which results when a second test potential $E_2$ is applied immediately after the first test potential $E_1$, is larger, which is supported by the terms in Eq. 3. However, if a sufficiently long second open-circuit potential is introduced allowing the accumulated reduced mediator at first electrode 166 to dissipate back into the bulk solution, then the initial current for the second test potential $E_2$ will be the same as the initial current for the first test potential $E_1$. Thus, if no reduced mediator is generated during the test time interval and there is a sufficiently long second open-circuit potential, then the current transient for the first and second test potentials will be the same.

Figure 10:
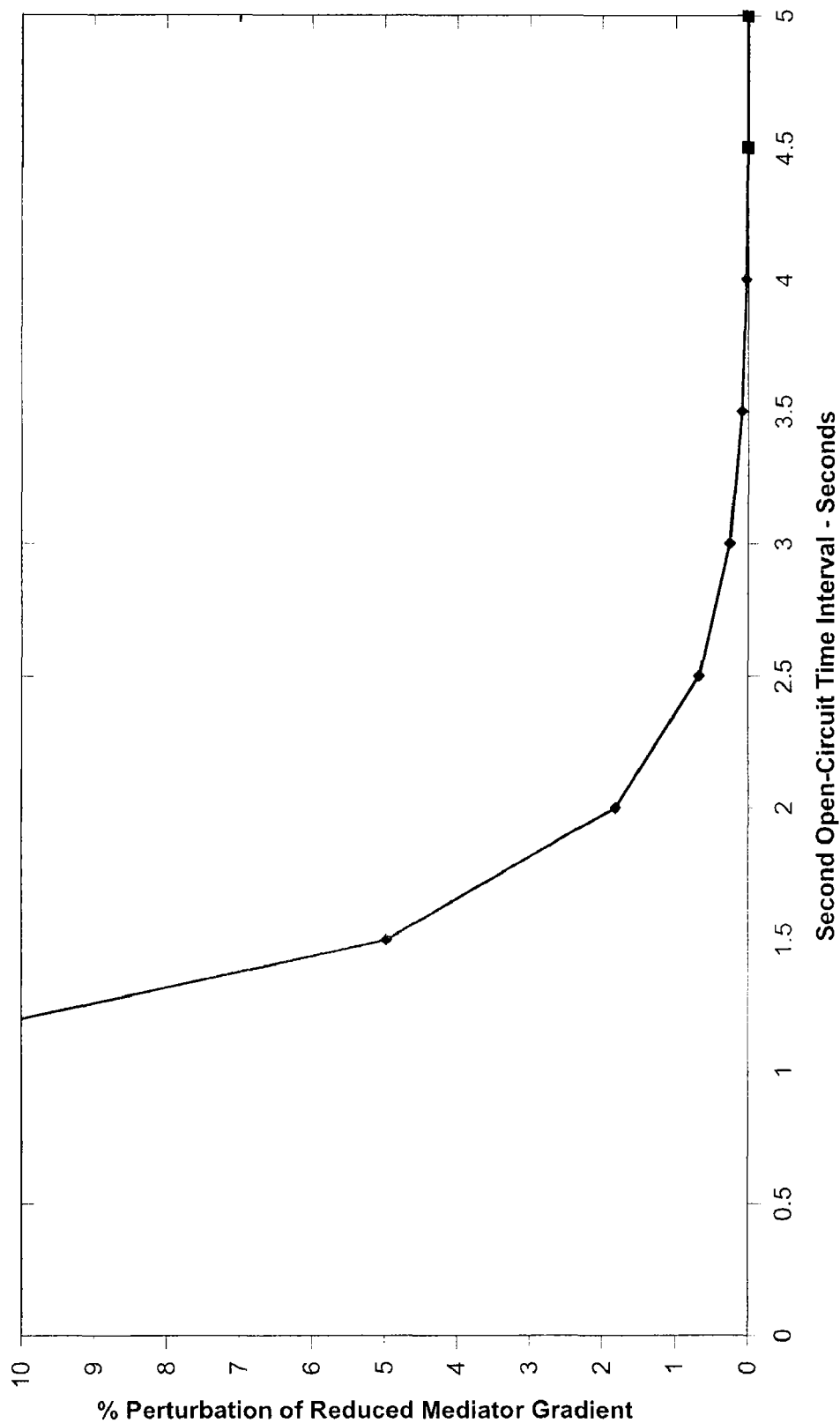
FIG. 10 is a chart showing the % perturbation of reduced mediator gradient on first electrode as a function of second open-circuit time interval.

The time required to allow reduced mediator to dissipate from first electrode 166 may be predicted using standard diffusion equations. In general, the fraction of reduced mediator which will dissipate at the surface of first electrode 166 is proportional to $$\exp\left(\frac{-4\pi^2 Dt}{L^2}\right)$$

as a function of time. As an example, it may be assumed that L is 95 microns and D is $4.5\times10^{-6}$ cm$^2$/s. FIG. 10 shows a graph indicating the % perturbation of the reduced mediator gradient as a function of the second open-circuit time interval. In this case, perturbation refers to the amount of reduced mediator which still needs to dissipate before the concentration of reduced mediator approaches the bulk concentration. Using the assumed parameters of L and D, about 2.5 seconds (i.e. $5\times L^2/(4\pi^2 D)$) will be required for the second open-circuit potential to be sufficiently long. In an embodiment of this invention, second open-circuit potential time interval may range from about 1 second to about 5 seconds, and preferably range from about 2 seconds to about 4 seconds. Depending on the parameters of a given test strip, one skilled in the art can easily determine what would be a sufficiently long open-circuit potential time interval such that the current transient for the first and second test potentials will be the same in the absence of a glucose reaction.

A simplified algorithm can be used for calculating a glucose concentration in the presence of interferents, when a sufficiently long open-circuit potential time interval is used as shown in Eq. 9.

$$[G]=\text{intercept}+\text{slope}\times(i_{pb}-i_{pa}) \quad \text{Eq. 9}$$

In Eq. 9, the intercept and slope are calibration factors. In this case, $i_{pb}$ will be proportional to the glucose concentration and interferent concentration and $i_{pa}$ will be proportional to the interferent concentration only. The difference between $i_{pb}$ and $i_{pa}$ will be a current that is proportional to glucose with a correction for interferents. Eq. 9 can be used when the electrochemical cell used to perform a test has co-planar electrodes.

Another simplified algorithm embodiment for calculating a glucose concentration in the presence of interferents with a sufficiently long open-circuit potential time interval is shown in Eq. 10.

$$[G]=\left(\frac{i_2}{i_3}\right)^p \times \{\text{intercept}+\text{slope}\ x\ (i_{pb}-i_{pa})\} \quad \text{Eq. 10}$$

Eq. 10 is similar to Eq. 9 except that it has a correction factor $$\left(\text{i.e.,}\ \left(\frac{i_2}{i_3}\right)^p\right)$$

to account for glucose reaction kinetics.

In another embodiment disclosed herein, test strips may be prepared for measuring hemoglobin in blood. In this embodiment, reagent layer 72 of a test strip 62 is replaced with a new reagent layer that contains ferricyanide and a lysing agent such as sodium deoxycholate. When the blood is dosed onto the new reagent layer, the red blood cells lyse allowing ferricyanide to oxidize hemoglobin. A description of a hemoglobin sensor can be found in U.S. Pat. No. 6,632,349 which is hereby incorporated by reference herein. The subsequently generated ferrocyanide can then be measured as a hemoglobin current. Similar to glucose, it is assumed that the ferrocyanide does not reach second electrode 164 during the initial stage of the assay. Once blood is detected in a test strip by a test meter, the test meter may serially apply a one second open-circuit potential, a 3 second first test potential of $-0.3$ V, and a 5 second test potential of $+0.3$ V.

The hemoglobin concentration H may be measured using a first hemoglobin algorithm as shown in the following Eq. 9.

$$H=\text{intercept}+\text{slope}\times C_o \quad \text{Eq. 9}$$

In this case, $C_o$ is proportional to the hemoglobin concentration and can be calibrated to a reference technique using standard regression analysis (slope and intercept). However, a modification to Eq. 9 can be made so that the hemoglobin assay can be performed accurately in the presence of interferents. Eq. 10 shows a second hemoglobin algorithm for improving the accuracy of a hemoglobin sensor.

$$H=\text{intercept}+\text{slope}\ x\ L\left\{\frac{i_{ssb}-i_{ssa}}{2FAD}\right\} \quad \text{Eq. 10}$$

where $i_{ssa}$ and $i_{ssb}$ are the steady-state currents from the first current transient and second current transients, respectively.

Example 1

A buffer was prepared that contained 67 mM citraconate at pH 6.8, 0.1% anti-foam (2 parts Pluronic P103 and 1 part Pluronic F87), 60 mM sucrose, and 1.7 mM CaCl$_2$. Next, GDH which used a PQQ cofactor, was added to the buffer so that it was 15 mg/mL. PQQ was then added to the buffer so that it could activate the GDH. After addition of PQQ, the formulation was allowed to incubate about on hour. Next, potassium ferricyanide was added to the mixture such that it was 600 mM. The formulation was striped onto first electrically conductive layer 66 as shown in FIG. 1 by means of a slot coating process which is described in U.S. Pat. Nos. 6,749,887; 6,689,411; and 6,676,995 which are hereby incorporated by reference herein. Upon coating the formulation and drying it such that it forms reagent layer 72, spacer 60, and second electrode 164 are assembled thereon to form test strip 62.

Example 2

Figure 11:
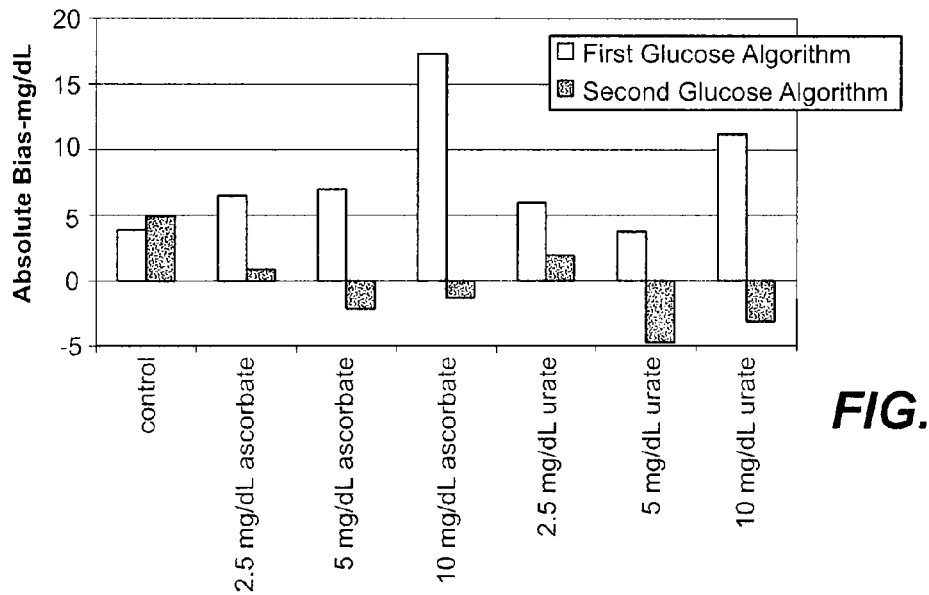
FIG. 11 is a chart showing the absolute bias in glucose results for a first glucose algorithm and a second glucose algorithm.

Several test strips 62 were tested with blood containing a glucose concentration ranging from about 83 to 88 mg/dL and had interferents spiked into the blood sample. Test strips 62 were tested on test meter 100 using a glucose test time interval $T_G$ of 5 seconds. Test meter 100 applied a potential waveform as shown in FIG. 6. A test current was collected for each test strip and converted to a glucose concentration using a first glucose algorithm, as shown in Eq. 1, and a second glucose algorithm, as shown in Eq. 6. An average bias was calculated for each test strip against the reference method in units of mg/dL. FIG. 11 shows that the overall bias was reduced in the presence of interferents such as ascorbate and urate when using the second glucose algorithm as opposed to using the first glucose algorithm.

Example 3

Figure 12:
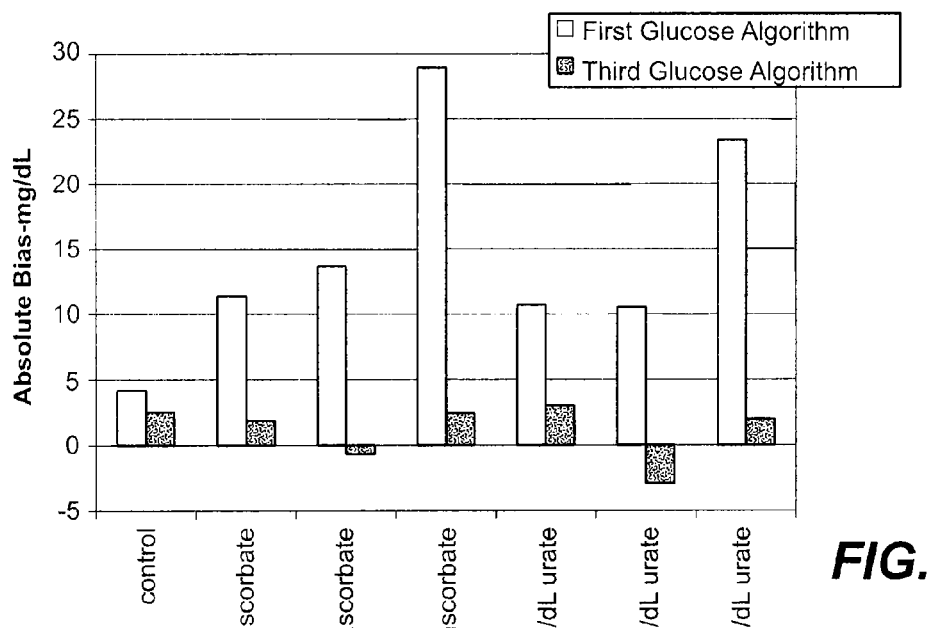
FIG. 12 is a chart showing the absolute bias in glucose results for first glucose algorithm and a third glucose algorithm.

The experiment of Example 3 was repeated in a similar manner with a different set of test strips 62. For this experiment, the test current was collected for each test strip and converted to a glucose concentration using a first glucose algorithm, as shown in Eq. 1, and a third glucose algorithm, as shown in Eq. 7. FIG. 12 shows that the overall bias was reduced in the presence of interferents when using the third glucose algorithm as opposed to using the first glucose algorithm. The use of the term $C_o$ instead of simple summation of current may enable a more accurate measurement to be made in the presence of interferents.

Example 4

Figure 13:
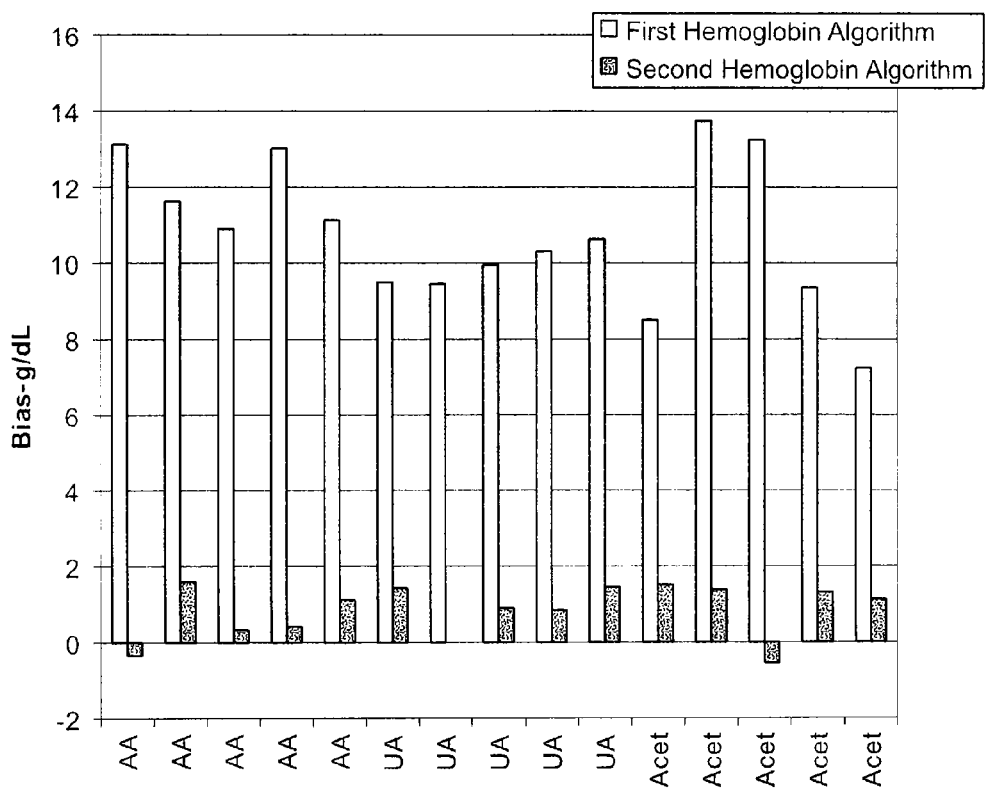
FIG. 13 shows an absolute bias for the concentration of hemoglobin in the presence of a particular interferent using a first hemoglobin algorithm and a second hemoglobin algorithm.

Several test strips 62 were prepared for the measurement of hemoglobin. Several test strips 62 were tested with blood containing a hemoglobin concentration of 16.3 g/dL, and had interferents spiked into the blood sample. A test current was collected for each test strip and converted to a hemoglobin concentration using a first hemoglobin equation, as shown in Eq. 9, and a second hemoglobin equation, as shown in Eq. 10. An average bias was calculated for each test strip against the reference method in units of g/dL. FIG. 13 shows that the overall bias was reduced in the presence of interferents such as ascorbate (AA=10 mg/dL), urate (UA=10 mg/dL), and acetaminophen (Acet=20 mg/dL) when using the second hemoglobin equation as opposed to using the first hemoglobin equation.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A method for reducing the effect of interferent in a test for analyte concentration, comprising:
    (a) introducing a physiological sample into an electrochemical cell, the electrochemical cell comprising:
        (i) first and second electrodes in a spaced apart relationship; and
        (ii) a first reagent;
    (b) applying a first test potential between said first and second electrodes, the first test potential having a first polarity and measuring cell current to obtain a first peak current value;
    (c) applying a second test potential between said first and second electrodes, the second test potential having a second polarity, and measuring cell current to obtain a second peak current value;
    (d) calculating an interference correction factor based on the first and second peak current values, wherein the interference correction factor can be used in a glucose concentration calculation to reduce the influence of chemical interferent compounds that will generate an interferent current by an oxidation or reduction reaction.

2. The method of claim 1, wherein the step (c) further includes measuring cell current as a function of time to obtain a second current transient and calculating a first current value based on the second current transient.

3. The method of claim 2, further comprising the step of calculating a corrected first current value by removing an interferent current value from the first current value.

4. The method of claim 3, wherein the step of calculating a corrected first current value includes multiplying the first current value by an interferent correction equation, wherein the interferent correction equation is $$\left\{ \frac{i_{pb} - 2i_{pa} + i_{ss}}{i_{pb} + i_{ss}} \right\}$$

where $i_{pb}$ is the first peak current value, $i_{pa}$ is the second peak current value, and $i_{ss}$ is a steady-state current value.

5. The method of claim 4, wherein the method further includes the steps of calculating a second current value based on the second current transient and measuring cell current as a function of time in step (b) to obtain a first current transient and calculating a third current value based on the first current transient.

6. The method of claim 5, further comprising the step of calculating an analyte concentration based upon an equation $$[C] = \left(\frac{i_2}{i_3}\right)^p \times (a \times i_4 - Z)$$

where [C] is an analyte concentration, $i_4$ is the first correct current value, $i_2$ is the second current value, $i_3$ is the third current value, and a, p, and Z are calibration factors.

7. The method according to claim 1, wherein the first reagent layer is disposed on the first electrode.

8. The method according to claim 7, wherein the first polarity is negative with respect to the second electrode and the second polarity is positive with respect to the second electrode.

9. The method according to claim 8, wherein a second reagent layer is disposed on the second electrode, wherein the second reagent layer comprises a redox mediator and is substantially free of the enzyme, and the redox mediator is capable of oxidizing an interferent present in the physiological sample.

10. The method of claim 1, wherein step (c) further includes measuring cell current as a function of time to obtain a second current transient.

11. The method of claim 1, wherein an analyte concentration is calculated based upon an equation $$[C] = \left(\frac{i_{ss}}{i_{pp}}\right)^P \times \left(C_o\left\{\frac{i_{pb} - 2i_{pa} + i_{ss}}{i_{pb} + i_{ss}}\right\} - Z\right)$$

where [C] is an analyte concentration, $i_{pp}$ is a current value derived from the second current transient, $C_G$ is an estimated glucose concentration, $i_{pa}$ is the first peak current value, $i_{pb}$ is the second peak current value, and $i_{SS}$ is a steady state current value and Z is a calibration factor.

12. The method of claim 11, wherein the term $i_{pp}$ is an average current over a short period of time near the end of the second current transient.

13. A method for reducing the effect of interferent in a test for analyte concentration, comprising:
  (a) introducing a physiological sample into an electrochemical cell, the electrochemical cell comprising:
    (i) a first reagent; and
    (ii) two or more electrodes, the two or more electrodes consisting of a single working electrode and one or more other electrodes in a spaced apart relationship;
  (b) applying a first test potential between the single working electrode and the one or more other electrodes, the first test potential having a first polarity, and measuring cell current to obtain a first peak current value;
  (c) applying a second test potential between the single working electrode and the one or more other electrodes, the second test potential having a second polarity, and measuring cell current to obtain a second peak current value;
  (d) calculating an interference correction factor based on the first and second peak current values, wherein the interference correction factor can be used in a glucose concentration calculation to reduce the influence of chemical interferent compounds that will generate an interferent current by an oxidation or reduction reaction.

14. The method of claim 13, wherein the two or more electrodes consist of a single working electrode and a single reference electrode.

* * * * *

UNITED STATES PATENT AND TRADEMARK OFFICE
CERTIFICATE OF CORRECTION

PATENT NO.           : 8,163,162 B2  
APPLICATION NO.      : 11/278341  
DATED                : April 24, 2012  
INVENTOR(S)          : Chatelier et al.

Page 1 of 1

It is certified that error appears in the above-identified patent and that said Letters Patent is hereby corrected as shown below:

Claims

Column 21, Claim 11, line 15, replace "$C_G$" with "$C_o$."

Signed and Sealed this  
Fifth Day of January, 2016

Michelle K. Lee  
*Director of the United States Patent and Trademark Office*